(12) United States Patent
Roberts et al.

(10) Patent No.: US 7,819,957 B2
(45) Date of Patent: Oct. 26, 2010

(54) OPERATING ROOM FILTER SYSTEMS

(76) Inventors: Keith Roberts, 7194-115th St. North, White Bear Lake, MN (US) 55110; David Rasch, 359 Parkview La., Maplewood, MN (US) 55119

( * ) Notice: Subject to any disclaimer, the term of this patent is extended or adjusted under 35 U.S.C. 154(b) by 609 days.

(21) Appl. No.: 11/801,045

(22) Filed: May 8, 2007

(65) Prior Publication Data

US 2007/0289449 A1   Dec. 20, 2007

Related U.S. Application Data

(60) Provisional application No. 60/813,422, filed on Jun. 14, 2006.

(51) Int. Cl.
*A61M 1/00* (2006.01)
*A62B 7/10* (2006.01)

(52) U.S. Cl. .......................... 96/132; 55/385.1; 55/472; 55/485; 55/486; 96/134; 96/135

(58) Field of Classification Search ............ 55/385.1, 55/472, 486, 356, 467, 485; 95/273, 140; 96/421, 422, 132, 135, 139, 152, 153, 131, 96/154, 134; 604/35
See application file for complete search history.

(56) References Cited

U.S. PATENT DOCUMENTS

| | | | | |
|---|---|---|---|---|
| 4,064,876 A * | 12/1977 | Mulchi | ............... | 128/206.15 |
| 4,141,703 A * | 2/1979 | Mulchi | ............... | 96/132 |
| 5,688,256 A | 11/1997 | Surrat et al. | ............... | 604/355 |
| 5,690,101 A * | 11/1997 | Kutta | ............... | 128/205.27 |
| 5,722,962 A | 3/1998 | Garcia | ............... | 604/264 |
| 5,942,017 A * | 8/1999 | Van Winkle, Sr. | ............... | 55/385.1 |
| 6,045,596 A * | 4/2000 | Holland et al. | ............... | 55/385.2 |
| 6,110,259 A * | 8/2000 | Schultz et al. | ............... | 95/273 |
| 6,428,612 B1 * | 8/2002 | McPhilmy et al. | ............... | 96/132 |
| 6,576,033 B1 | 6/2003 | Booth | ............... | 55/485 |
| 6,589,316 B1 * | 7/2003 | Schultz et al. | ............... | 95/273 |
| 6,592,543 B1 * | 7/2003 | Wortrich et al. | ............... | 604/35 |
| 6,746,504 B2 * | 6/2004 | Booth | ............... | 55/485 |
| 6,773,477 B2 * | 8/2004 | Lindsay | ............... | 55/385.3 |
| 6,881,236 B2 * | 4/2005 | Schultz et al. | ............... | 55/385.1 |
| 7,597,731 B2 * | 10/2009 | Palmerton et al. | ............... | 55/385.1 |
| 2003/0200738 A1 * | 10/2003 | Booth | ............... | 55/485 |
| 2005/0102981 A1 * | 5/2005 | Schultz et al. | ............... | 55/385.1 |
| 2007/0137484 A1 * | 6/2007 | Roberts | ............... | 95/273 |
| 2009/0288561 A1 * | 11/2009 | Palmerton et al. | ............... | 96/417 |

OTHER PUBLICATIONS

*Smoke Production and Smoke Reduction in Endoscopic Surgery: Preliminary Report* by Dr. Douglas Ott, Date unknown.
*Balston Adsorbents Used in Type CI Cartridges.* (date unknown).
*Carboxyhemoglobinemia Due to Peritoneal Smoke Absorption from Laser Tissue Combustion at Laparoscopy* (Nov. 6, 1998.

* cited by examiner

*Primary Examiner*—Duane Smith
*Assistant Examiner*—Minh-Chau T Pham
(74) *Attorney, Agent, or Firm*—Jacobson & Johnson

(57) ABSTRACT

An operating room filter system connectable to a surgical body gas evacuator, such as a trocar, that includes a carbon monoxide filter media that removes carbon monoxide from a surgical waste gas. In addition, the inclusion of further filter media upstream of the carbon monoxide filter media inhibits the saturation of the carbon monoxide filter media to thereby provide an extended life to the filtration system.

11 Claims, 2 Drawing Sheets

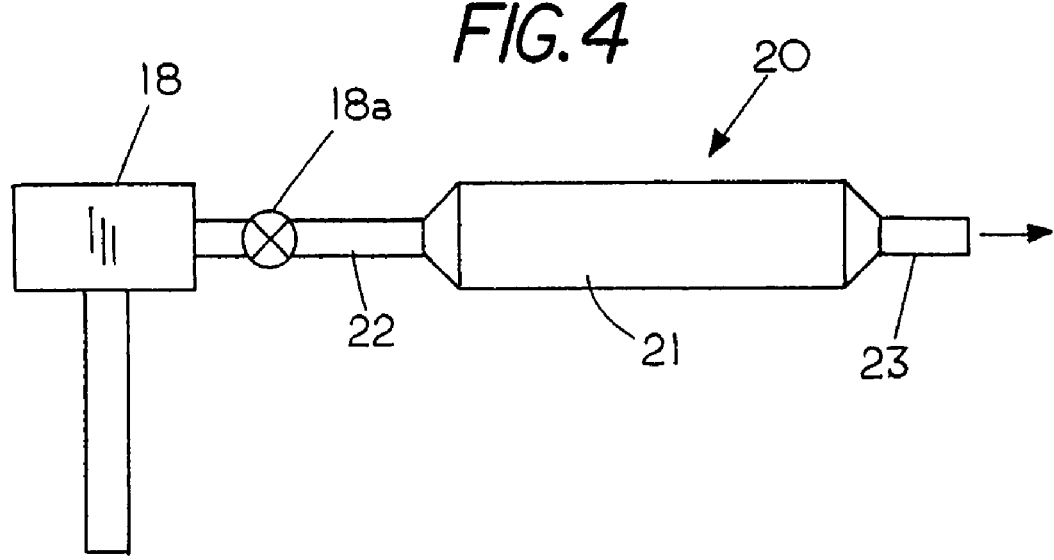
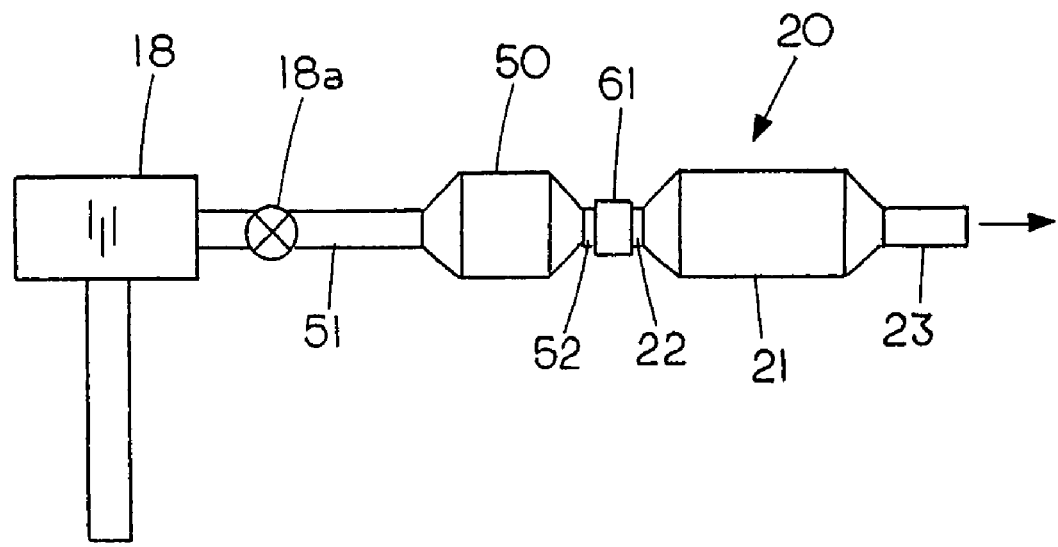

OPERATING ROOM FILTER SYSTEMS

CROSS REFERENCE TO RELATED APPLICATIONS

This application claims priority from provisional patent application Ser. No. 60/813,422 filed Jun. 14, 2006.

FIELD OF THE INVENTION

This invention relates generally to filter systems and, more specifically, to operating room filter systems that can remove an unwanted gas from a surgical waste gas generated during a surgical procedure.

STATEMENT REGARDING FEDERALLY SPONSORED RESEARCH OR DEVELOPMENT

None

REFERENCE TO A MICROFICHE APPENDIX

None

BACKGROUND OF THE INVENTION

One of the problems with surgical procedures, such as laparoscopic surgery and the like, is the disposal of surgical waste gas generated during the surgical procedure. Douglas Ott of Georgia Biomedical addressed the contamination of the insufflation gases directed into a body cavity with a $CO_2$ Guard Filter, which is a 0.2 um particulate filter that is used to filter the insufflation gas injected into a body cavity during surgery. Others have addressed the problems with surgical waste gas generated in a body cavity during the surgical procedure. These surgical waste gases, which can contain harmful materials, are often discharged directly into the operating room prior to or at completion of the surgical procedure.

It is known that smoke created during surgical procedures and subsequently discharged into the operating room as part of the surgical waste gas poses a health problem for operating room staff. The smoke can result in infections, lesions on the throat and nose, as well as health problems associated with the inhalation of noxious gases such as carbon monoxide, acid gases including formic acid, and hydrocarbon vapors such as formaldehyde, which are present in the smoke. Smoke evacuators have been used by surgeons and operating room staff members for both general surgery and laparoscopic surgeries to address the problem of discharging surgical waste gas containing smoke.

While surgeons have vented the surgical waste gas from the peritoneum directly into the operating room without filtering it Dr. Joxel Garcia in U.S. Pat. No. 5,722,962, discloses a trocar mounted filter to address the venting of surgical waste gas from the peritoneum into the operating room with the trocar mounted filter including two filter elements to remove large and small particles from the surgical waste gas. Surratt et al in U.S. Pat. No. 5,688,256, also discloses an invention that controls the flow rate of the surgical waste gas exiting the peritoneum while also filtering the surgical waste gas.

The above identified particle filters do not address the contamination associated with odors in the surgical waste gas. However, U.S. Pat. Nos. 6,110,259 and 6,589,316, Schultz disclose a smoke evacuator filter with a particulate filter media in addition to an odor removing media. Schultz acknowledges that smoke odor can also be a problem for surgical staff and or staff members. Schultz addresses the issue of odor removal through the use of activated carbon. Similarly, in U.S. Pat. No. 6,576,033, Booth discloses a Filter for Use in Medical Procedures that uses an activated carbon bed to remove odors associated with laser surgery.

A study entitled *Smoke Production and Smoke Reduction in Endoscopic Surgery: Preliminary Report* by Dr. Douglas Ott, identified a list of toxic chemicals generated by pyrolysis of protein and lipids during laser surgery including: Acroloin, acetronitrile, acrylonitrile, acetylene, alkyl benzenes, benzene, butadiene, butene, carbon monoxide, creosols, ethane, ethane, ethylene, formaldehyde, free radicals, hydrogen cyanide, isobutene, methane, pheonal, PAH's, propene, propylene, pyridene, pyrrole, styrene, toluene and xylene.

These chemicals are considered to be toxic by various agencies including NIOSH<EPS, ACGIH and OSHA. Odor removing media referenced by the above identified prior art includes activated carbon, which will remove most "$C_4$ and heavier hydrocarbons, ketones, alcohols, esters, ethers, organic acids and chlorinated organics, Freons, all aromatic hydrocarbons, carbon disulfide". Little or no adsorption with activated carbon occurs on organic compounds lighter than $C_3$. These chemicals include "carbon monoxide, amines, ammonia, acetylene, most C and lighter hydrocarbons, sulfur dioxide." Molecular Sieve Type 4A will remove carbon dioxide, ammonia, sulfur dioxide, hydrogen sulfide, acetylene, propylene, methane, ethane, water vapor, ethylene, ethylene dioxide, carbon disulfide. Molecular Sieve Type 13X is recommended for the removal of methanol, straight chain mercaptans, Freon 11, Freon 12, Freon 114, sulfur hexafluoride, straight chain hydrocarbons to $C_{22}$, cyclohexane, diphenyl, butene-1, isopentane, benzene, toluene, xylene, boron tridfloride, triethylamine and smaller amines. Calgon Type GHR Sulfur Impregnated Carbon is recommended for the removal of mercury vapor. Sodium and Calcium Hydroxide is recommended for the removal of all acidic gases. See *Balston Adsorbents Used in Type C1 Cartridges*. Acid gases can also be present in which case, (a mixture of calcium and sodium hydroxide) can be used.

Carbon monoxide is a colorless, odorless, poisonous gas the significance of the surgical waste gas can be overlooked. As a result what has been failed to be addressed in the above inventions is the removal of an odorless, poisonous gases such as carbon monoxide from the surgical waste gas. Dr. Douglas Ott provides a study entitled *Carboxyhemoglobinemia Due to Peritoneal Smoke Absorption from Laser Tissue Combustion at Laparoscopy*. Ott points out that carbon monoxide is a respiratory poison that can directly affect the respiratory system by absorption of carbon monoxide gas. Carbon monoxide is known as a byproduct of incomplete combustion of a carbon containing material. In the Ott study, smoke was sampled on the exhaust side of a trocar. Two minutes after laser surgery, intra-abdominal carbon monoxide increased to 425 ppm. The peak concentration observed was 60 times the recommended exposure limit by the EPA.

Currently carbon monoxide gas from the surgical waste gas is discharged into the operating room without any means of removing the carbon monoxide gas from the operating room although other contaminants are removed from the surgical waste gas before discharging the surgical waste gas into the operating room. The invention described herein addresses the problem of removal of carbon monoxide from a surgical waste gas before the surgical waste gas is vented to the operating room.

SUMMARY OF THE INVENTION

The invention comprises an operating room filter system connectable to a surgical body gas evacuator, such as a trocar, that includes a carbon monoxide filter media that removes carbon monoxide from a surgical waste gas. In addition, the inclusion of a filter media upstream of the carbon monoxide filter media inhibits the saturation of the carbon monoxide filter media to thereby provide an extended life to the filter system.

BRIEF DESCRIPTION OF THE DRAWINGS

FIG. 4 shows the filter system connected to a trocar to vent surgical waste gasses into the operating room atmosphere; and FIG. 5 shows the filter system with a particle filter and the carbon monoxide filter connected to a trocar that vents surgical waste gas into the operating room atmosphere.

DESCRIPTION OF THE PREFERRED EMBODIMENT

Figure 1:
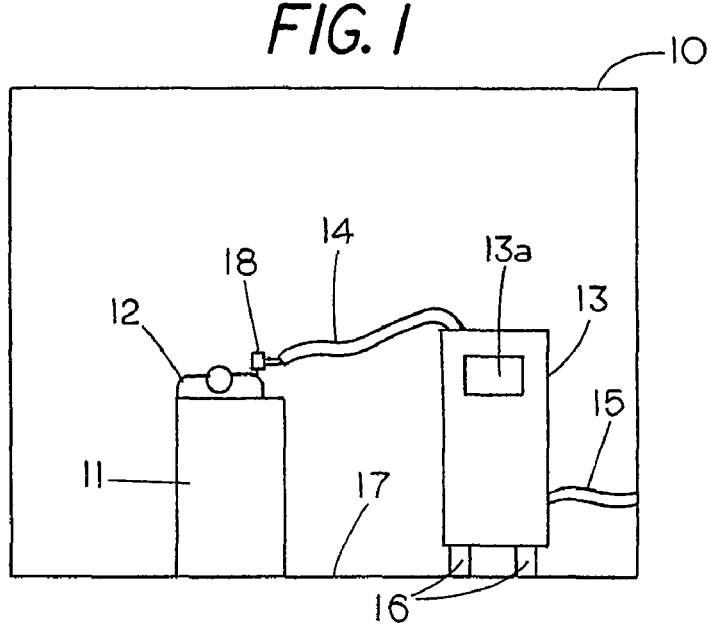
FIG. 1 is a schematic view of an operating room with an evacuator for removing unwanted gasses and odors present during an operation procedure.

FIG. 1 shows a schematic view of an operating room 10 with a patient 12 on an operating table 11. An insufflator apparatus 13 supported on wheels 16 rests on the floor 17 of the operating room. The insufflation apparatus connects to a power source through cable 15 and includes a hose 14 for directing hydrated insulation gas, such as carbon dioxide, through a device such as a trocar 18 and into a body cavity of patient 12 on operating room table 11. The insufflation apparatus 13 is known in the art and are more fully described in Douglas Ott. U.S. Pat. Nos. 6,068,609 and 5,411,474. Insufflation apparatus 13 includes a control panel 13a to allow an operator to control the dispensing of the insufflation gas into the body cavity. Typically, the patient is undergoing surgery such as a laparoscopic surgery where bone or tissue is being cut while the patient can also be receiving an insufflation gas through trocar 18. Laparoscopic surgeries are procedures whereby surgeons are able to perform surgeries that heretofore, required cutting the abdominal cavity to obtain access to the peritoneal cavity. For example, in laparoscopic surgery a small incision is made in the abdomen prior to the surgery and the trocar is inserted into the abdomen through the small incision. A tube 14 is attached to the trocar 18 that carries the insufflation gas, typically carbon dioxide gas, into the body cavity in order to keep the body 12 in an inflated condition. Once the medical procedure is nearing completion the carbon dioxide insufflation gas as well as all the other contaminates generated in the body cavity during the medical procedure are vented into the operating room atmosphere as a surgical waste gas.

One of the devices for removing gas borne particles from the surgical waste gas is shown in Garcia U.S. Pat. No. 5,722,962. Garcia uses two filter elements connected to a trocar fitting to remove unwanted particle contaminants before the surgical waste gas is discharged into the operating room. While the gas borne particles, such as bacteria, virus, body fluids and the like can be removed by the particle filter media the common combustion gas that occurs as a result of the surgical procedure, namely carbon monoxide, flows through the particle filters and directly into the operating room when the surgical waste gas is vented from the body cavity. As carbon monoxide is a harmful gas the invention described herein removes the carbon monoxide gas before discharging the surgical waste gas into the operating room.

FIG. 4 shows apparatus for removing carbon monoxide gas from a surgical waste gas generated during a medical procedure. The system includes a body evacuation device, such as a trocar 18, connected to a filter system 20. A valve 18a on trocar 18a allows one to vent the surgical waste gas from a body cavity through a device such as trocar 18 and into the filter system 20. That is, the surgical waste gas flows through trocar 18, conduit 22 through filter 21 and then vents to the operating room atmosphere through outlet 23. During the passage of the surgical waste gas through the filter 21 a filter media therein removes the carbon monoxide from the surgical waste gas.

FIG. 5 shows a filter system 20 for removing carbon monoxide gas from a surgical waste gas generated during a medical procedure including a particle filter 50 located upstream of the filter 21. In this embodiment the surgical waste gas flows from the trocar 18 through valve 18a, through tubing 51 and then into the particle filter 50 to remove unwanted contaminates from the surgical waste gas before the surgical waste gas enters the filter 21. An outlet 52 connects to inlet 22 of filter 21 through a flexible coupling to permit flow from filter 50 to filter 21. The surgical waste gas with particle contaminates removed therefrom by filter 50 then flows through conduit 52 into the filter system 20 that includes a filter 21 that contains a filter media 29 for removing unwanted carbon monoxide gas from the surgical waste gas.

The invention described herein addresses the issue of removal of containments including odorless and acidic gases such as carbon monoxide as well as formic acid, but is not limited to these surgical waste gases. To remove carbon monoxide gas, a commercially available carbon monoxide filter media such as hopcalite is incorporated in filter 21 for the removal of carbon monoxide. However, other adsorbents can also be used for the removal of carbon monoxide from surgical waste gas. For example, adsorbents such as Molecular Sieve Type 4A, Type 13X and calcium and sodium hydroxide can also be used to remove gases currently unaddressed by the use of a filter containing an activated carbon.

Figure 2:
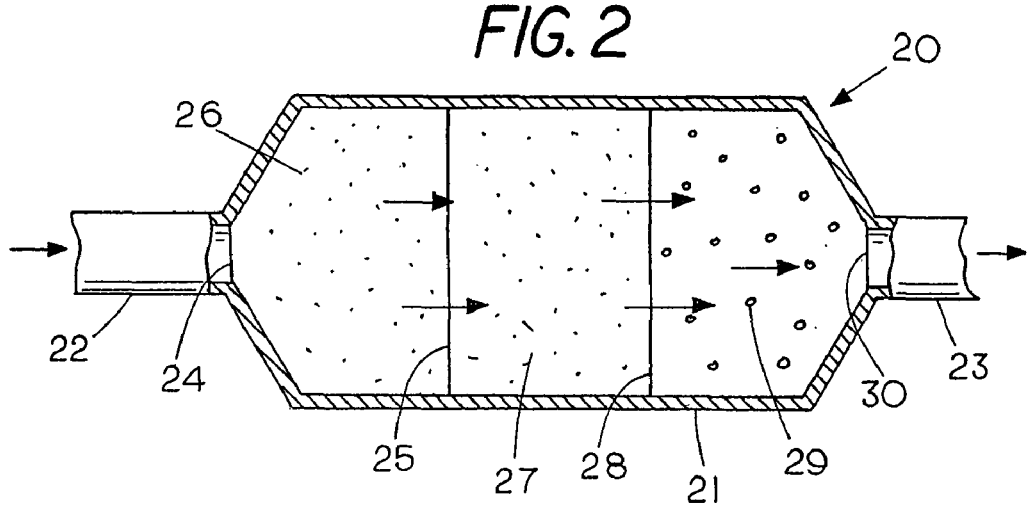
FIG. 2 is a section view of an inline filter for use with the evacuator of FIG. 1.

FIG. 2 shows a disposable filter system 20 for use in the removal of unwanted gases and odors. Filter 21 comprises a housing having a fluid inlet 22 and a fluid outlet 23. A first gas permeable screen 24 that allows gas to flow threrethrough is located on one side of a filter media 26 and a second gas permeable screen 25 is located on the opposite side of filter media 26 for the purposes of maintaining the filter media 26 in position for surgical waste gas to flow threrethrough.

Located downstream of filter media 26 is a water removable material or moisture absorbent filter media 27. An example of a commercially available desiccant for removal of water is silica gel. Moisture absorbent material 27 is retained on one side by gas permeable screen 25 and on the opposite side by gas permeable screen 28 to thereby hold the filter media 27 in position as the surgical waste gas flows threrethrough.

Located downstream of moisture absorbent filter media 27 is a carbon monoxide filter media 29 which is bounded on one side by gas permeable screen 28 and on the other side by gas permeable screen 30. Thus, in the filter system 20 the surgical waste gas flows through filter media 26, moisture absorbent filter media 27 and carbon monoxide filter media 29, which removes the carbon monoxide, before the surgical waste gas is discharged into the operating room.

While filter 21 with a carbon monoxide filter media could be coupled directly to the trocar 18 it is preferred to position the carbon monoxide filter media 29 downstream of a moisture absorbent filter media 27 in order to extend the life of the carbon monoxide filter media 29 by preventing saturation of the carbon monoxide filter media. In addition, by incorporating a filter media to remove formaldehyde, such as activated charcoal, one can remove formaldehyde upstream of the carbon monoxide filter media 29, to further extend the life of the carbon monoxide filter media 29.

In the filtration system 20, an odor-removing filter media such as an activated carbon filter media 26 upstream of the carbon monoxide filter media 29 to remove formaldehyde and other gases that can consume the carbon monoxide filter media are located as part of a single filter 21.

A benefit of locating the carbon monoxide filter media 29 downstream of the moisture adsorbent filter media 27 is that one is able to extend the life the carbon monoxide filter media 29 by reducing the dew point and moisture vapor content of the surgical waste gas flowing through the carbon monoxide filter media.

Filter media to reduce the dew point of the gas prior to contact with the carbon monoxide filter media typically include water vapor removers such as molecular sieves, silica gel or activated alumina. Other types of devices to reduce the dew point of the surgical waste gas can also be utilized. For example, devices such as refrigerated air dryers, condensers, heat exchangers, membrane air dryers and other types of compressed air dryers.

Formic acid may also be present in the surgical waste gas. Vapor adsorbents such as activated carbon can also absorb some of formic acid, but it may be beneficial to incorporate an acid-scrubbing desiccant such as a mixture of sodium and calcium hydroxide. Should an acid-scrubbing filter media be included as part of filter 21, it is beneficial to configure the acid-scrubbing filter media upstream or prior to the moisture-removing filter media to avoid premature saturation of the moisture removing filter media.

A feature of the filtration system 20 is that it allows one to quickly connect to existing portable smoke evacuators that vent gasses to an operating room atmosphere through the use of standard tubing.

In the embodiment shown in FIG. 2 the incoming surgical waste gas enter inlet 22, flows through screen 24 and into the carbon filter media 26. After removal of odors and other materials the surgical waste gas flows through the activated charcoal or carbon filter media 26. The surgical waste gas, which contains carbon monoxide, flows though the moisture reducing filter media 27, which reduces the moisture content of the surgical waste gas. Once the surgical waste gas containing the carbon monoxide enters the carbon monoxide filter media 29 the carbon monoxide is removed by the filter media 29 and the remaining surgical waste gas is either directed to a further filter or is vented to the operating room. A feature of he filtrations system 20 of FIG. 2 is that it can be quickly and easily connected to other systems through the use of flexible tubing couplings 22 and 23.

Figure 3:
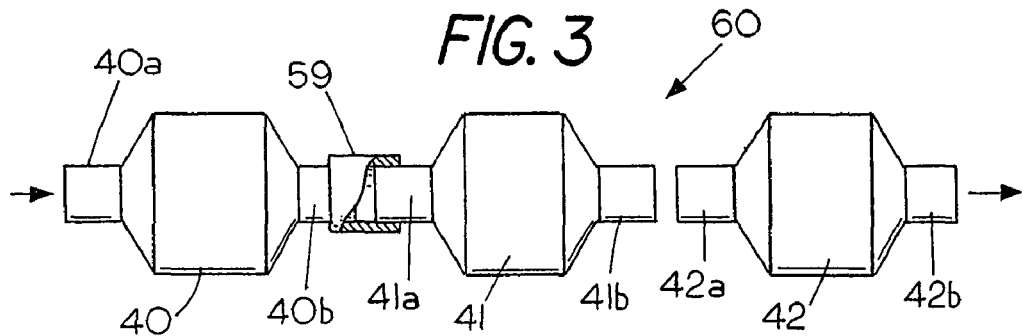
FIG. 3 is a front view of three filters that can be interchangeably ganged to together to remove unwanted gasses and odors from an operating room.

FIG. 3 shows an alternate embodiment of a filtration system 60 comprising a set of three gangable filters, a first filter 40, a second filter 41 and a third filter 42. Each of filters 40, 41, and 42 has a fluid inlet on one side and a fluid outlet on the opposite side.

Filter 40 includes an inlet 40a and an outlet 40b, which is shown coupled to inlet 41a through a flexible tubing coupling. Filter 40 contains a single filter media such as carbon or activated charcoal. The filter 41 contains a single filter media such as a moisture removal filter media and filter 42 contains a single filter media such as a carbon monoxide filter media that removes carbon monoxide from the surgical waste gas.

In operation the fluid outlet 40b of filter 40 connects to filter inlet 41a of filter 41 and the filter outlet 41b connects to the fluid inlet 42a of filter 42 through a coupling (not shown) to provide a ganged arrangement of filters that are individually changeable. For example filter 40 can contain a filter media such as activated charcoal, filter 41 can contain a water vapor remover such as a descant or the like and filter 42 can contain a carbon monoxide filter media such as sodium hydroxide and calcium hydroxide. During the filtration of the surgical waste gas if one or more of the filters is spent the filter can be replaced with a fresh filter.

Thus, the invention includes the method of discharging surgical waste gas into an operating room atmosphere comprising the steps of: directing the surgical waste gas through a carbon monoxide filter media before discharging the surgical waste gas into the operating room atmosphere. To enhance the life of the carbon monoxide filter media one can include the step of directing the surgical waste gas through a vapor removal filter media before directing the surgical waste gas through the carbon monoxide filter media. To remove particles in the surgical waste gas one can direct the surgical waste gas through a particle filter before directing the surgical waste gas through the carbon monoxide filter media. To remove formaldehyde from the surgical waste gas one can direct the surgical waste gas through a formaldehyde filter media before directing the surgical gas into the carbon monoxide filter media.

We claim:

1. A filter for use during and after surgical procedures to receive the surgical waste gas generated during a medical procedure comprising:
    a trocar for venting a surgical waste gas from a body cavity, wherein the surgical waste gas includes both moisture and carbon monoxide;
    a particle filter connected to said trocar;
    an inlet for receiving a surgical waste gas and an outlet for discharging the surgical waste gas;
    a carbon monoxide filter media positioned to cause the surgical waste gas to flow therethrough thereby removing carbon monoxide from the surgical waste gas before the surgical waste gas is discharged into the operating room;
    a moisture absorbent filter media for removing moisture from the surgical waste gas, said moisture absorbent material located downstream of said inlet and upstream of said carbon monoxide filter media to absorb moisture in the surgical waste gas prior to the surgical waste gas flowing through said carbon monoxide filter media to thereby inhibit moisture saturation of said carbon monoxide filter, said moisture absorbent material contained on one side by a first gas permeable screen and on an opposite side by a second gas permeable screen;
    a carbon filter media, said carbon filter media located upstream of said carbon monoxide filter media for removal of odors from the surgical waste gas prior to removal of moisture from the surgical waste gas.

2. The surgical waste gas filter system of claim 1 wherein each of the filter media are contained in a single housing.

3. The surgical waste gas filter system of claim 2 wherein the trocar includes a valve therein.

4. The filter of claim 1 wherein the particle filter is located upstream of the carbon filter media.

5. An inline extended life surgical waste gas filter system for trapping contaminants and removing carbon monoxide gas comprising:
- a trocar for venting a surgical waste gas from a body cavity, wherein the surgical waste gas include both moisture and carbon monoxide;
- a housing having a fluid inlet and a fluid outlet with said fluid inlet connected to said trocar to direct the surgical waste gas into the fluid inlet of said housing;
- a carbon monoxide filter media located in said housing for capturing carbon monoxide from the surgical waste gas, said carbon monoxide filter media located proximate said fluid outlet;
- a moisture absorbent filter media located in said housing for removing moisture from the surgical waste gas, said moisture absorbent material located upstream of said carbon monoxide filter media to absorb moisture in the surgical waste gas prior to the surgical waste gas flowing through said carbon monoxide filter media to thereby inhibit moisture saturation of said carbon monoxide filter;
- a first gas permeable screen separating said moisture absorbent material in said housing from said carbon monoxide filter media in said housing with said first gas permeable screen located upstream of said carbon monoxide filter media to maintain the moisture absorbent material separate from the carbon monoxide filter media;
- a carbon filter media located in said housing with said carbon filter media located upstream of said carbon monoxide filter media for removal of odors from the surgical waste gas prior to removal of moisture from the surgical waste gas;
- a second gas permeable screen separating said moisture absorbent material filter media from said carbon filter media to cause the surgical waste gas to first pass through the carbon filter media and the moisture absorbent material before passing through the carbon monoxide filter media to thereby discharge the surgical waste gas therefrom without the contaminants trapped by said filter system.

6. The surgical waste gas filter system of claim 5 wherein the carbon filter media comprises activated charcoal.

7. The surgical waste gas filter system of claim 6 wherein the moisture absorbing filter media is selected from the group consisting of molecular sieve, activated alumina, and silica gel.

8. The surgical waste gas filter system of claim 7 wherein the filter system includes at least one upstream filter media that removes contaminants selected from the group consisting of smoke, particulate matter, hydrocarbon vapors, acid gases, organic odor, hydrocarbons, and moisture vapor.

9. The surgical waste gas filter system of claim 8 wherein the carbon monoxide filter media comprises hopcalite.

10. The surgical waste gas filter system of claim 5 wherein each of the filter media are contained in a gangable separate housing.

11. The surgical waste gas filter system of claim 5 including a particle filter.

* * * * *